United States Patent [19]

Weller, III et al.

[11] Patent Number: 5,236,916
[45] Date of Patent: Aug. 17, 1993

[54] OXADIAZINONE SUBSTITUTED INDOLE AND BENZIMIDAZOLE DERIVATIVES

[75] Inventors: Harold N. Weller, III, Pennington; Michael A. Poss, Lawrenceville, both of N.J.

[73] Assignee: E. R. Squibb & Sons, Inc., Princeton, N.J.

[21] Appl. No.: 889,010

[22] Filed: May 26, 1992

[51] Int. Cl.$^5$ ................ C07D 413/06; A61K 31/535
[52] U.S. Cl. .................................. 514/229.2; 544/68
[58] Field of Search ....................... 544/68; 514/229.2

[56] References Cited

FOREIGN PATENT DOCUMENTS

| | | |
|---|---|---|
| 2027839 | 4/1991 | Canada . |
| 2033121 | 6/1991 | Canada . |
| 412848 | 2/1990 | European Pat. Off. . |
| 411766 | 2/1991 | European Pat. Off. . |
| 429257 | 5/1991 | European Pat. Off. . |

OTHER PUBLICATIONS

J. H. Freeman et al., "1,2,4-Benzothiadiazine Dioxides and 3,4-Dihydro-3,4-Dihydro-1,2,4-Benzothiadiazine Dioxides", J. Org. Chem. 16, 815 (1951).

K. S. Atwal et al., "Substituted 1,4-Dihydropyrimidines, 3. Synthesis of Selectively Functionalized 2-Hetero-1,4-dihydropyrimidines", J. Org. Chem. 54, 25 (1989), pp. 5898-5907.

Primary Examiner—John M. Ford
Attorney, Agent, or Firm—Ellen K. Park

[57] ABSTRACT

Novel compounds having the formula

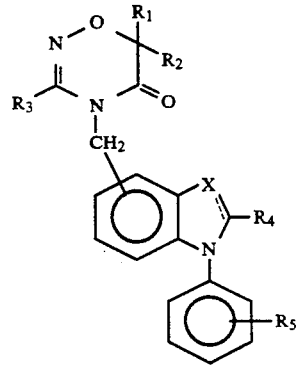

wherein X, $R_1$, $R_2$, $R_3$, $R_4$ and $R_5$ are as defined herein. These compounds inhibit the action of angiotensin II and are useful, therefore, for example, as antihypertensive agents.

8 Claims, No Drawings

OXADIAZINONE SUBSTITUTED INDOLE AND BENZIMIDAZOLE DERIVATIVES

FIELD OF THE INVENTION

The present invention relates to novel substituted biphenyl derivatives useful as antihypertensive agents.

SUMMARY OF THE INVENTION

In accordance with the present invention, novel compounds which inhibit the action of the hormone angiotensin II are disclosed. These compounds are of the general formula

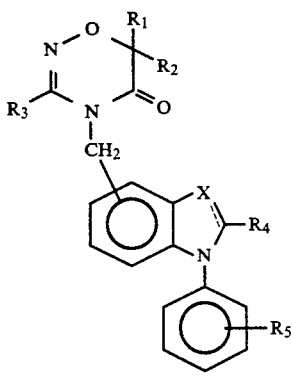

and pharmaceutically acceptable salts and prodrugs thereof.

As used in formula I, and throughout the specification, the symbols have the following meanings:

X is —N— or

the broken line adjacent to the X atom represents the optional presence of a double bond, provided that if X is nitrogen, the double bond must be present;

$R_1$ and $R_2$ are each independently hydrogen, alkyl, aryl, arylalkyl, cycloalkyl, cycloalkylalkyl, thiophenylalkyl, pyridylalkyl or —$R_{12}CO_2R_{13}$;

$R_3$ is hydrogen, alkyl, alkenyl, alkynyl, arylalkyl, —$OR_{16}$ or —$SR_{16}$ bonded to the ring system by a single bond or $R_3$ is O or S bonded to the ring system by a double bond to form a carbonyl or thiocarbonyl group;

$R_4$ and $R_4'$ are independently selected from hydrogen, alkyl, aryl, cycloalkyl, arylalkyl, haloalkyl,

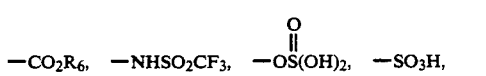

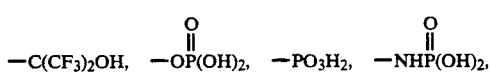

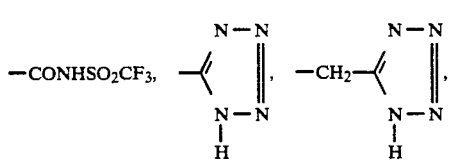

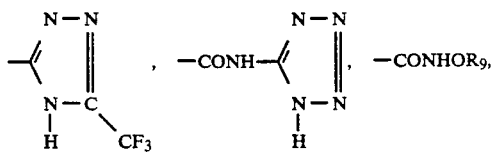

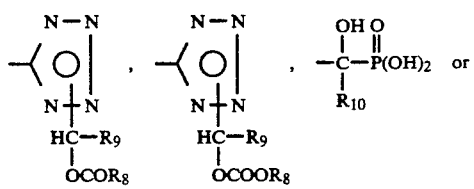

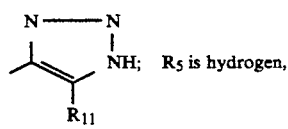

$R_5$ is hydrogen,

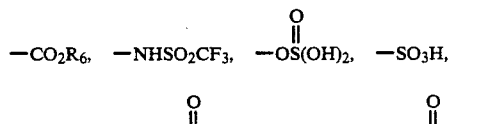

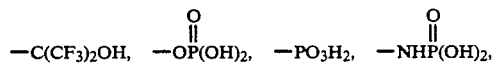

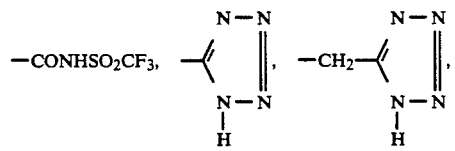

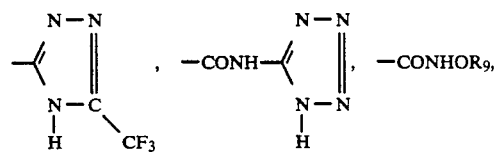

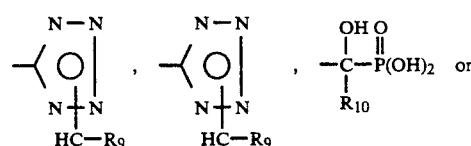

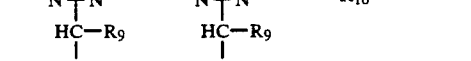

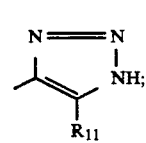

$R_6$ is hydrogen, alkyl, perfluoroalkyl of 1 to 8 carbon atoms, cycloalkyl of 3 to 6 carbon atoms, phenyl, benzyl,

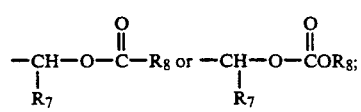

$R_7$ is hydrogen, alkyl, perfluoroalkyl, cycloalkyl, phenyl or benzyl;

$R_8$ is alkyl, aryl, alkylaryl, arylalkyl or cycloalkyl;

$R_9$ is hydrogen, alkyl, aryl, alkylaryl, arylalkyl or cycloalkyl;

$R_{10}$ is hydrogen, alkyl of 1 to 5 carbon atoms or phenyl;

$R_{11}$ is —CH, —NO$_2$ or —CO$_2$R$_6$;

$R_{12}$ is a single bond, alkyl, alkenyl, aryl or arylalkyl;

$R_{13}$ is hydrogen, alkyl, cycloalkyl, aryl, arylalkyl,

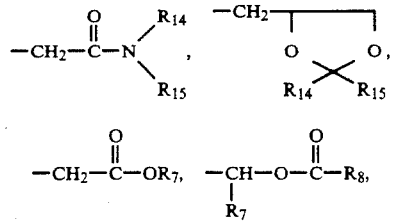

alkali metal or ammonium;

$R_{14}$ and $R_{15}$ are each independently hydrogen, alkyl, cycloalkyl, aryl or arylalkyl, Or $R_{14}$ and $R_{15}$ together are —(CH$_2$)$_m$— or —CH$_2$—CH=CH—CH$_2$—;

$R_{16}$ is hydrogen, alkyl, alkenyl, alkynyl, aryl or arylalkyl; and m is an integer of 2 to 5.

DETAILED DESCRIPTION OF THE INVENTION

The present invention relates to the compounds of formula I (and pharmaceutically acceptable salts and prodrugs thereof), to pharmaceutical compositions employing such compounds and to methods of using such compounds. Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain groups having 1 to 10 carbon atoms. Alkyl groups having 1 to 4 carbon atoms are preferred.

The term "alkenyl" and "alkynyl" refer to both straight and branched chain groups. Those groups having 2 to 10 carbon atoms are preferred.

The term "cycloalkyl" refers to groups having 3 to 8 carbon atoms.

The term "alkoxy" refers to groups having 1 to 8 carbon atoms. Alkoxy groups having 1 to 3 carbon atoms are preferred.

The term "halogen" refers to fluorine, chlorine, bromine and iodine with fluorine and chlorine being preferred.

The term "aryl" refers to phenyl or naphthyl or phenyl or naphthyl substituted with substituents selected from halogen, alkyl, alkoxy, carboxy, alkylthio, hydroxy, alkanoyl, nitro, amino, alkylamino, dialkylamino or trifluoromethyl groups. Preferred aryl groups are phenyl and monosubstituted phenyl and phenyl is most preferred.

All stereoisomers of the compounds of the instant invention are contemplated, either in admixture or in pure or substantially pure form.

It should be understood that the present invention includes prodrug forms, such as ester, acetal and/or mixed acetal derivatives of the compounds of formula I. For example, such derivatives have been documented in *Design of Prodrugs*, edited by H. Bundgard, (Elsevier, 1985) and *Methods in Enzymology*, Vol. 42, p. 309-396, edited by K. Widder et al. (Academic Press, 1985). Further, it is understood that any moiety at R$_4$ and/or R$_5$ that will be cleaved in vivo to provide an acidic R$_4$ and/or R$_5$ moiety is within the spirit and scope of this invention.

An exemplary process for preparing the compounds of formula I includes coupling an oxadiazinone of the formula

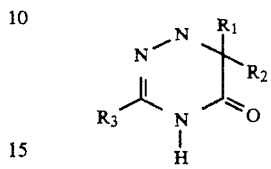

with an indole of the formula III

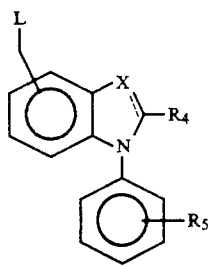

wherein L is a leaving group such as a halogen, in the presence of a coupling agent such as cesium carbonate, in an organic solvent such as dimethylformamide.

Compounds of formula II are prepared by converting a nitrile of the formula IV

such as valeronitrile to a corresponding amidoxime by treatment with hydroxylamine in an aqueous alcohol solvent (e.g., methanol) at a temperature of from about 40° C. to about 60° C. to form an amidoxime of formula V

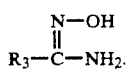

Compound V reacts with an alkylating agent of formula VI

(wherein Y is alkyl, aryl, or aralkyl and Y' is a leaving group such as bromine, chlorine, methanesulfonate, trifluoromethane sulfonate, and the like) in the presence of a base (e.g., sodium methoxide) in an organic solvent (e.g., methanol) to form an amine-ester of formula VII

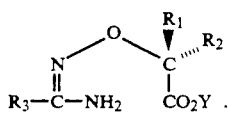

Amine-ester VII may react upon heating at a temperature from about 90° C. to about 110° C. or may be treated with a base or catalyst (e.g., trimethylaluminum) in an organic solvent or solvent mixture (e.g., methylene chloride/hexane) to form an oxadiazinone of formula VIII

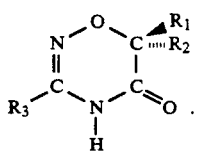

Compounds of formula III where X is

can be prepared by coupling a compound of the formula IX

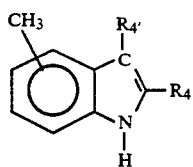

with a compound of the formula X

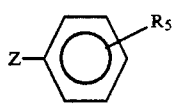

where Z is bromide in a polar solvent such as pyridine in the presence of a catalyst such as copper oxide, to provide compounds of the formula XI

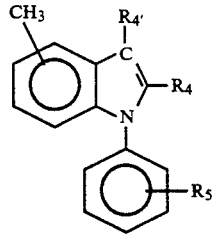

A leaving group, L, for example, a halogen can be added by known methodology to provide compounds of the formula XII

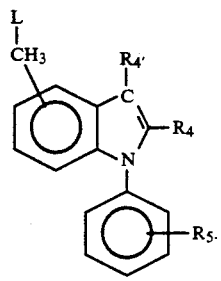

Compounds of formula IX can be prepared by known techniques such as those described in *J. Heterocyclic Chem.*, 25, 1 (1988).

Compounds of formula III where X is

or X is nitrogen may also be prepared by reacting a compound of the formula XIII

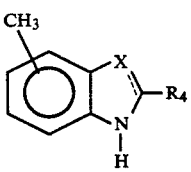

with a compound of the formula XIV

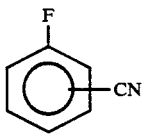

in the presence of a base such as potassium carbonate in an organic solvent such as dimethylformamide, to provide a compound of the formula XV

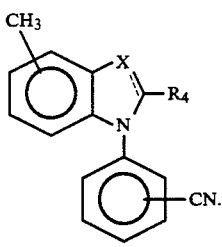

Compound XV can thereafter be treated with a brominating agent such as N-bromosuccinimide and a radical initiator such as 2,2'-azobisisobutyronitrile, in an organic solvent such as carbon tetrachloride, to provide a compound of the formula XVI

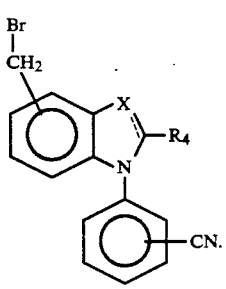

Intermediate XVI can be coupled with the oxadiazinone of formula II to provide XVII

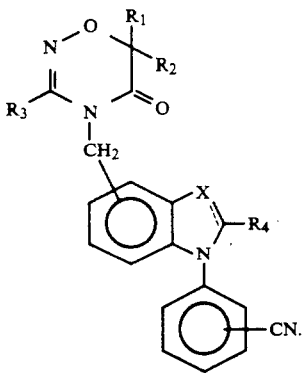

Compound XVII can then be reacted with an azide such as tributyltinazide to provide compounds of formula I where X is nitrogen and R$_5$ is

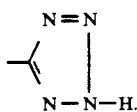

Compounds of formula I where X is nitrogen and R$_5$ is other than

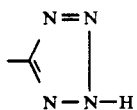

can be prepared by using intermediate X (Z=F) in place of compound XIV above.

Compounds of formula XIII where X is nitrogen are prepared as described by Mathias et al., *Synthetic Communications*, 5, 461–469 (1975). Compounds of formulae X and XIV are commercially available.

When preparing the compounds of the instant invention wherein the substituent groups contain one or more reactive functionalities such as hydroxy, amino, tetrazolyl, carboxyl, mercapto or imidazolyl groups, it may be necessary to protect these groups during the reactions in which they are used. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred compounds of the present invention are those wherein

X is

where
R$_4$' is hydrogen;
R$_1$ is hydrogen;
R$_2$ is arylalkyl;
R$_3$ is alkyl;
R$_4$ is hydrogen; and
R$_5$ is ortho-tetrazolyl.

The present compounds of formula I inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to A-II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. The compounds of this invention are also useful in the treatment of congestive heart failure and cardiac hypertrophy. In addition, in view of the role of these compounds in the renin-angiotensin system described above, the A-II antagonist compounds disclosed herein are also expected to be useful for the same or similar indications which have developed for ACE inhibitors.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE

3-Butyl-5,6-dihydro-6-(2-phenylethyl)-4-[[1-[2-(1H-tetrazol-5-yl)phenyl]-1H-indol-4-yl]methyl]-4H-1,2,4-oxadiazin-5-one, monopotassium salt

A. N-Hydroxypentanimidamide

Compound A was prepared by procedures adapted from *Chem. Rev.* 62, 155 (1962) and *Cancer Res.* 38, 1291 (1978).

Sodium carbonate solid (13 g, 123 mmol) was added to a suspension of hydroxylamine hydrochloride (16.7 g, 240 mmol) in methanol (120 mL) and water (60 mL). Gas evolution was observed and a clear solution resulted. Valeronitrile (25 mL, 240 mmol) was then added and the mixture was stirred at 50° C. for 17 hours, after which most of the methanol was removed by distillation in vacuo. The aqueous residue was extracted with dichloromethane (three times); the extract was dried (magnesium sulfate) and concentrated to give compound A as a colorless oil, which solidified on storage at $-30°$ C. (10.4 g, 37%).

B. 3-Butyl-6-(2-Phenylethyl)-4H-1,2,4-oxadiazin-5(6H)-one

Ethyl-2-bromo-4-phenylbutanoate (1.694 g, 6.25 mmol) was added to a mixture of compound A (581 mg, 5 mmol) and cesium carbonate (3.258 g, 10 mmol) in dimethylformamide (5 mL), and stirred at room temperature for 18 hours. The mixture was poured into water (300 mL), extracted with ethyl acetate (3×200 mL), dried (magnesium sulfate), and concentrated in vacuo to provide the intermediate 2-[[(1-Aminopentylidene)amino]oxyl]-4-phenyl-butanoic acid, methyl ester as an amber oil. The crude intermediate was dissolved in methylene chloride (25 mL) under argon, and a solution of trimethyl aluminum in hexane (20 mL of a 2.0M solution, 40 mmol) was added. The resulting mixture was stirred 2.5 hours, after which it was poured into 0.5N hydrochloric acid (300 mL), and extracted with methylene chloride (3×300 mL). The crude extract was purified using flash chromatography, (200 g silica gel eluted with 4:1 hexane:ethyl acetate) dried, and concentrated to give the title compound as a yellow waxy solid (594 mg, 2.28 mmol, 46%); m.p. 75°-77° C.

C. 1H-Indole-4-carboxylic acid, methyl ester

To a solution of indole-4-carboxylic acid (506 mg, 3.14 mmol) dissolved in a mixture of methanol (5 mL) and diethyl ether (10 mL) was added ethereal diazomethane until disappearance of starting acid was indicated by TLC. Anhydrous magnesium sulfate was then added and the solution filtered and concentrated in vacuo. Flash chromatography on 10 g of Merck silica gel eluted with 2:1, chloroform:hexanes, followed by 10:1, chloroform:diethyl ether afforded the title compound (540 mg, 98%).

D. 1-(2-Cyanophenyl)-1H-indole-4-carboxylic acid, methyl ester

A mixture of the title C compound (40.6 mg, 0.232 mmol), 2-fluorobenzonitrile (38 μL, 0.348 mmol), potassium carbonate (64.1 mg, 0.464 mmol), and 18-crown-6 (6.1 mg, 0.0232 mmol) in 0.23 mL of dimethylformamide was heated at 150° C. for 150 minutes. Upon cooling to room temperature, the reaction mixture was diluted with ethyl acetate, filtered and rinsed with pH 4 buffer. The aqueous layer was further extracted with two more portions of ethyl acetate and the combined organic extract was rinsed with brine, dried over sodium sulfate, filtered through magnesium sulfate and concentrated in vacuo. Flash chromatography on 5 g of Merck silica gel eluted with 5:1, chloroform: hexanes, followed by 100% chloroform afforded the title compound (61.6 mg, 96%).

E. 1-(2-Cyanophenyl)-1H-indole-4-carboxylic acid

The title D compound (8.0 g, 28.95 mmol), 1N sodium hydroxide(43.4 mL, 43.4 mmol), methanol (43.4 mL) and tetrahydrofuran (43.4 mL) were combined and heated to 50° C. After 4 hours 40 minutes, the reaction was cooled to room temperature and 10% hydrochloric acid ($-50$ mL) was added to precipitate a white solid. The mixture was filtered and the product was collected as a white solid (7.2 g, 95%).

F. 2-[4-(Hydroxymethyl)-1H-indol-1-yl]benzonitrile

Borane-tetrahydrofuran complex (1M in tetrahydrofuran, 27.3 mL) was added to a solution of the title E compound (7.17 g, 27.3 mmol) in tetrahydrofuran (distilled, 27.3 mL) at $-20°$ C., warmed to room temperature and stirred for 21 hours. The solution was cooled to 0° C. and quenched with 1N sodium hydroxide to pH=14. The solution was extracted with ether (3×100 mL), washed with sodium chloride, dried over magnesium sulfate, filtered and concentrated to a light green solid. The solid was recrystallized twice from ethyl acetate/hexane to yield the title compound (5.54 g, 82%).

G. 2-[4-(Bromomethyl)-1H-indol-1-yl]benzonitrile

To a solution of the title F compound (5.46 g, 22 mmol) in methylene chloride (distilled, mL) at 0° C. was added carbon tetrabromide (10.2 g, 30.8 mmol) and triphenylphosphine (7.5 g, 28.6 mmol). The reaction was stirred for 15 minutes at 0° C. and was then warmed to room temperature. After 2.5 hours, the reaction was diluted in methylene chloride and placed directly on a Merck silica gel column (66 g) eluting with (1:1) toluene/hexane for purification. The product fractions were collected and concentrated, then triturated with cold ethyl acetate to obtain the title compound (5.8 g, 85%).

H. 2-[4-[[3-Butyl-5,6-dihydro-5-oxo-6-(2-phenylethyl)-4H-1,2,4-oxadiazin-4-yl]methyl]-1H-indol-1-yl]benzonitrile A mixture of the title B compound (260 mg, 1.2 mmol), the title G compound (311 mg, 1 mmol), cesium carbonate (652 mg, 2 mmol) and dimethylformamide (5 mL) was stirred under argon at room temperature for 18 hours. The mixture was poured into water (200 mL), extracted with ethyl acetate, dried (magnesium sulfate) and concentrated in vacuo to an amber oil. The crude residue was purified by flash chromatography (65 g silica gel eluted with 4:1 hexane:ethyl acetate) to provide the title compound as a colorless oil (373 mg, 0.76 mmol, 76%).

I.

3-Butyl-5,6-dihydro-6-(2-phenylethyl)-4-[[1-[2-(1H-tetrazol-5-yl)phenyl]-1H-indol-4-yl]methyl]-4H-1,2,4-oxadiazin-5-one, monopotassium salt A solution of the title H compound (345 mg, 0.7 mmol) and tributyltinazide (700 mg, 2.11 mmol) in xylenes (0.5 mL) was refluxed for sixteen hours, cooled to room temperature and purified by flash chromatography (65 g silica gel eluted with 60:40:1 hexane:ethyl acetate:acetic acid). The fractions containing the major UV absorbing product were combined, concentrated in vacuo, dissolved in absolute ethanol (20 mL), adjusted to pH 10 using an aqueous solution of potassium carbonate (5%), and purified using preparative HPLC (Jordi-gel polystyrene column eluted with a water to methanol gradient, UV detection at 254 nanometers). HPLC fractions containing the major product were combined, concentrated in vacuo, dissolved in ethanol (5 mL) and water (25 mL) filtered through a five micron filter and lyophilized to provide the title compound as a white solid (138 mg, 0.22 mmol, 32%); m.p. 125°–130° C.

What is claimed is:

1. A compound of the formula

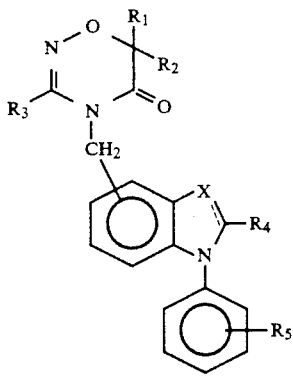

or a pharmaceutically acceptable salt or prodrug thereof;

wherein X is —N— or

the broken line adjacent to the X atom represents the optional presence of a double bond, provided that if X is nitrogen, the double bond must be present;

$R_1$ and $R_2$ are each independently hydrogen, alkyl, aryl, arylalkyl, cycloalkyl, cycloalkylalkyl, thiophenylalkyl, pyridylalkyl or $-R_{12}CO_2R_{13}$;

$R_3$ is hydrogen, alkyl, alkenyl, alkynyl, arylalkyl, $-OR_{16}$ or $-SR_{16}$ bonded to the ring system by a single bond or $R_3$ is O or S bonded to the ring system by a double bond to form a carbonyl or thiocarbonyl group;

$R_4$ and $R_4'$ are independently selected from hydrogen, alkyl, aryl, cycloalkyl, arylalkyl, haloalkyl, $-CO_2R_6$, $-NHSO_2CF_3$, $-OS(OH)_2$, $-SO_3H$, $-C(CF_3)_2OH$, $-OP(OH)_2$, $-PO_3H_2$, $-NHP(OH)_2$, $-CONHSO_2CF_3$,

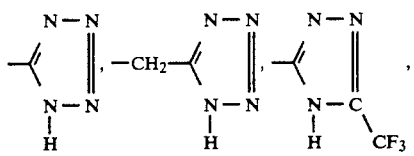

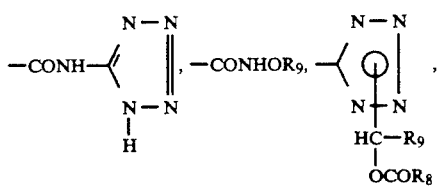

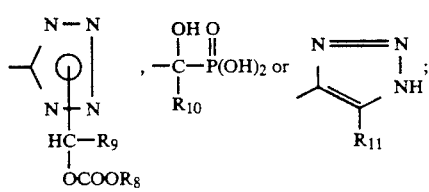

$R_5$ is hydrogen, $-CO_2R_6$, $-NHSO_2CF_3$, $-OS(OH)_2$, $-SO_3H$, $-C(CF_3)_2OH$, $-OP(OH)_2$, $-PO_3H_2$, $-NHP(OH)_2$, $-CONHSO_2CF_3$,

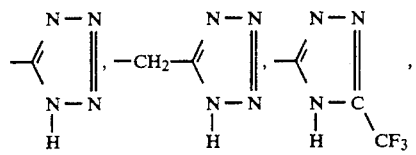

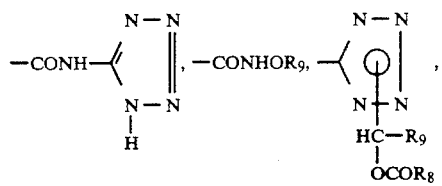

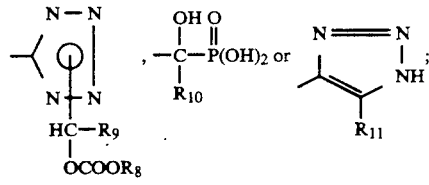

$R_6$ is hydrogen, alkyl, perfluoroalkyl of 1 to 8 carbon atoms, cycloalkyl of 3 to 6 carbon atoms, phenyl, benzyl, $$-\underset{R_7}{CH}-O-\overset{O}{\underset{\|}{C}}-R_8 \text{ or } -\underset{R_7}{CH}-O-\overset{O}{\underset{\|}{C}}OR_8;$$

$R_7$ is hydrogen, alkyl, perfluoroalkyl, cycloalkyl, phenyl or benzyl;

$R_8$ is alkyl, aryl, alkylaryl, arylalkyl or cycloalkyl;

$R_9$ is hydrogen, alkyl, aryl, alkylaryl, arylalkyl or cycloalkyl;

$R_{10}$ is hydrogen, alkyl or 1 to 5 carbon atoms or phenyl;

$R_{11}$ is —CN, —NO$_2$ or —CO$_2$R$_6$;

$R_{12}$ is a single bond, alkyl, alkenyl, aryl or arylalkyl;

$R_{13}$ is hydrogen, alkyl, cycloalkyl, aryl, arylalkyl,

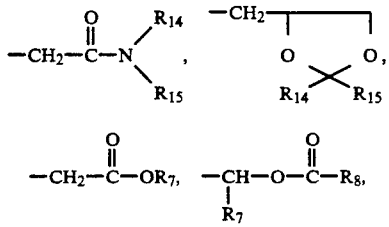

alkali metal or ammonium;

$R_{14}$ and $R_{15}$ are each independently hydrogen, alkyl, cycloalkyl, aryl or arylalkyl, or $R_{14}$ and $R_{15}$ together are -(CH$_2$)$_m$— or —CH$_2$—CH=CH—CH$_2$—;

$R_{16}$ is hydrogen, alkyl, alkenyl, alkynyl, aryl or arylalkyl;

m is an integer of 2 to 5;

the term "alkyl" refers to both straight and branched chain groups having 1 to 10 carbon atoms:

the term "alkenyl" and "alkynyl" refer to both straight and branched chain groups having 2 to 10 carbon atoms; and the term "aryl" refers to phenyl or naphthyl or phenyl or naphthyl substituted with halogen, alkyl, alkoxy, carboxy, alkylthio, hydroxy, alkanoyl, nitro, amino, alkylamino, dialkylamino or trifluoromethyl groups.

2. A compound of claim 1 wherein
X is

where $R_4'$ is hydrogen;

$R_1$ is hydrogen;

$R_2$ is arylalkyl;

$R_3$ is alkyl;

$R_4$ is hydrogen; and $R_5$ is ortho-tetrazolyl.

3. The compound of claim 1, wherein one of $R_1$ and $R_2$ is arylalkyl.

4. A compound of claim 1, 3-Butyl-5,6-dihydro-6-(2-phenylethyl)-4-[[1-[2-(1H-tetrazol-5-yl)phenyl]-1H-indol-4-yl]methyl[-4H-1,2,4-oxadiazin-5-one, monopotassium salt, or a pharmaceutically acceptable salt or prodrug thereof.

5. A pharmaceutical composition comprising a compound of claim 1 and a pharmaceutically acceptable carrier.

6. A method for treating hypertension comprising administering to a mammalin specie in need thereof a therapeutically effective amount of a composition of claim 5.

7. A method for treating congestive heart failure comprising administering to a mammalin specie in need thereof a therapeutically effective amount of a composition of claim 5.

8. A method for preventing cardiac hypertrophy comprising administering to a mammalin specie in need thereof a therapeutically effective amount of a composition of claim 5.

* * * * *